(12) United States Patent
Allen et al.

(10) Patent No.: US 6,683,106 B2
(45) Date of Patent: Jan. 27, 2004

(54) N-(INDOLE-2-CARBONYL)-B-ALANINAMIDE CRYSTAL FORMS

(75) Inventors: Douglas J. M. Allen, New London, CT (US); Frank R. Busch, Gales Ferry, CT (US); Joseph F. Krzyzaniak, Pawcatuck, CT (US); Zheng Jane Li, Quaker Hill, CT (US); Susan L. Orrill, Gales Ferry, CT (US); Peter R. Rose, Ledyard, CT (US); Derek L. Tickner, Waterford, CT (US); Harry O. Tobiassen, Ledyard, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/413,772

(22) Filed: Apr. 15, 2003

(65) Prior Publication Data

US 2003/0195243 A1 Oct. 16, 2003

Related U.S. Application Data

(60) Provisional application No. 60/349,525, filed on Apr. 15, 2002.

(51) Int. Cl.[7] .................. C07D 209/10; A61K 31/403; A01N 43/38
(52) U.S. Cl. .................. 514/414; 548/491; 548/492
(58) Field of Search ................ 514/414; 548/491, 548/492

(56) References Cited

U.S. PATENT DOCUMENTS

| | | | |
|---|---|---|---|
| 6,107,329 A | 8/2000 | Hoover et al. | 514/415 |
| 6,277,877 B1 | 8/2001 | Hoover et al. | 514/415 |
| 6,297,269 B1 | 10/2001 | Hulin et al. | 514/414 |

*Primary Examiner*—Joseph K. McKane
*Assistant Examiner*—Andrea D. Small
(74) *Attorney, Agent, or Firm*—Peter C. Richardson; Gregg C. Benson; Carl J. Goddard

(57) ABSTRACT

The instant invention provides crystal forms of 5-chloro-N-[(1S,2R)-3-[3R,4S]-3,4-dihydroxy-1-pyrrolidinyl]-2-hydroxy-3-oxo-1-(phenyl) methyl)propyl]-1H-indole-2-carboxamide (I)

(I)

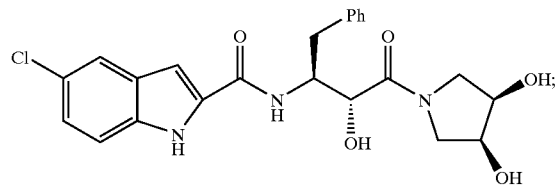

processes for the production of such crystal forms; pharmaceutical compositions comprising such crystal forms; and methods of treating glycogen phosphorylase dependent diseases, or conditions with such crystal forms, or such pharmaceutical compositions.

12 Claims, 7 Drawing Sheets

N-(INDOLE-2-CARBONYL)-B-ALANINAMIDE CRYSTAL FORMS

CROSS REFERENCE TO RELATED APPLICATION

This application claims the benefit of U.S. Provisional Application No. 60/349,525 filed Apr. 15, 2002.

FIELD OF THE INVENTION

The invention relates to crystal forms of 5-chloro-N-[(1S, 2R)-3-[3R,4S]-3,4-dihydroxy-1-pyrrolidinyl]-2-hydroxy-3-oxo-1-(phenylmethyl)propyl]-1H-indole-2-carboxamide; processes for the production thereof; pharmaceutical compositions thereof; and methods of treating glycogen phosphorylase dependent diseases, or conditions, therewith.

BACKGROUND OF THE INVENTION

Despite the early discovery of insulin and its subsequent widespread use in the treatment of diabetes, and the later discovery of, and use of, sulfonylureas (e.g. Chlorpropamide™ (Pfizer), Tolbutamide™ (Upjohn), Acetohexamide™ (E. I. Lilly), Tolazamide™ (Upjohn), and biguanides (e.g. Phenformin™ (Ciba Geigy), and Metformin™ (G. D. Searle)) as oral hypoglycemic agents, therapeutic regimens for the treatment of diabetes remain less than satisfactory. The use of insulin, necessary in about 10% of diabetic patients in which synthetic hypoglycemic agents are not effective (Type 1 diabetes, insulin dependent diabetes mellitus), requires multiple daily doses, usually by self-injection. Determination of the proper dosage of insulin requires frequent estimations of sugar levels in the urine or blood. The administration of an excess dose of insulin causes hypoglycemia, with effects ranging from mild abnormalities in blood glucose to coma, or even death. Treatment of non-insulin dependent diabetes mellitus (Type 2 diabetes) usually consists of a combination of diet, exercise, oral agents, e.g., sulfonylureas, and, in more severe cases, insulin. However, clinically available hypoglycemic agents can have other side effects that limit their use. In any event, where one of these agents may fail in an individual case, another may succeed. A continuing need for hypoglycemic agents, which may have fewer side effects or succeed where others fail, is clearly evident.

Atherosclerosis, a disease of the arteries, is recognized to be the leading cause of death in the United States and Western Europe. The pathological sequence leading to atherosclerotic development and occlusive heart disease is well known. The earliest stage in this sequence is the formation of "fatty streaks" in the carotid, coronary, and cerebral arteries, and in the aorta. These lesions are yellow in color due to the presence of lipid deposits found principally within smooth-muscle cells and in macrophages of the intima layer of the arteries and aorta. It is further postulated that most of the cholesterol found within the fatty streaks, in turn, gives rise to development of the so-called "fibrous plaque", which consists of accumulated intimal smooth muscle cells laden with lipid and surrounded by extra-cellular lipid, collagen, elastin, and proteoglycans. These cells, plus matrix, form a fibrous cap that covers a deeper deposit of cell debris and more extra cellular lipid, which comprises primarily free and esterified cholesterol. The fibrous plaque forms slowly, and is likely in time to become calcified and necrotic, advancing to the so-called "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, medical professionals have placed renewed emphasis on lowering plasma cholesterol levels, and low density lipoprotein cholesterol in particular, as an essential step in prevention of CVD. The upper limits of so-called "normal" cholesterol are now known to be significantly lower than heretofore appreciated. As a result, large segments of Western populations are now recognized to be at particular high risk. Such independent risk factors include glucose intolerance, left ventricular hypertrophy, hypertension, and being male. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (high blood pressure) is a condition that occurs in the human population as a secondary symptom to various other disorders such as renal artery stenosis, pheochromocytoma, or endocrine disorders. However, hypertension is also evidenced in many patients in whom the causative agent, or disorder, is unknown. While such essential hypertension is often associated with disorders such as obesity, diabetes, and hypertriglyceridemia, the relationship between these disorders has not been elucidated. Additionally, many patients present with symptoms of high blood pressure in the complete absence of any other signs of disease, or disorder.

It is known that hypertension can directly lead to heart failure, renal failure, and stroke, which conditions are all capable of causing short-term death. Hypertension also contributes to the development of atherosclerosis, and coronary disease, which conditions gradually weaken a patient and can lead, in long-term, to death.

The precise etiology of essential hypertension is unknown, although a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in vascular constriction, and genetic pre-disposition.

The treatment of essential hypertension has been undertaken bearing the foregoing factors in mind. Thus, a broad range of β-blockers, vasoconstrictors, angiotensin converting enzyme (ACE) inhibitors, and the like have been developed and marketed as antihypertensive agents. The treatment of hypertension utilizing such agents has proven beneficial in the prevention of short-interval deaths such as heart failure, renal failure, and brain hemorrhaging (stroke). However, the development of atherosclerosis, or heart disease due to hypertension over a long period of time, remains a problem. This implies that, although high blood pressure is being reduced, the underlying cause of essential hypertension remains unresponsive to this treatment.

Hypertension has further been associated with elevated blood insulin levels, a condition known as hyperinsulinemia. Insulin, a peptide hormone whose primary actions are to promote glucose utilization, protein synthesis, and the formation and storage of neutral lipids, also acts, inter alia, to promote vascular cell growth and increase renal sodium retention. These latter functions can be accomplished without affecting glucose levels and are known causes of hypertension. Peripheral vasculature growth, for example, can cause constriction of peripheral capillaries; while sodium retention increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion which can occur in both out-patient and perioperative settings. There is currently an unmet medical need to prevent or minimize adverse myocardial perioperative outcomes, particularly perioperative myocardial infarction. Both cardiac and non-cardiac surgery are associated with substantial risks for myocardial infarction or death, and some 7 million patients undergoing non-cardiac surgery are considered to be at risk, with incidences of perioperative death and serious cardiac complications as high as 20–25% in some instances. In addition, of the 400,000 patients undergoing coronary by-pass surgery annually, perioperative myocardial infarction is estimated to occur in 5% and death in 1–2%. There is currently no commercial drug therapy in this area which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients. The mechanism(s) responsible for the myocardial injury observed after ischemia and reperfusion is not fully understood, however, it has been reported (M. F. Allard, et al. Am. J. Physiol., 267, H66–H74, (1994) that pre-ischemic glycogen reduction is associated with improved post-ischemic left ventricular functional recovery in hypertrophied rat hearts.

Hepatic glucose production is an important target for Type 2 diabetes therapy. The liver is the major regulator of plasma glucose levels in the post absorptive (fasted) state, and the rate of hepatic glucose production in Type 2 diabetes patients is significantly elevated relative to normal individuals. Likewise, in the postprandial (fed) state, where the liver has a proportionately smaller role in the total plasma glucose supply, hepatic glucose production is abnormally high in Type 2 diabetes patients.

Glycogenolysis is an important target for interruption of hepatic glucose production. The liver produces glucose by glycogenolysis (breakdown of the glucose polymer glycogen) and gluconeogenesis (synthesis of glucose from 2- and 3-carbon precursors). Several lines of evidence indicate that glycogenolysis may make an important contribution to hepatic glucose output in Type 2 diabetes. First, in normal post absorptive man, up to 75% of hepatic glucose production is estimated to result from glycogenolysis. Second, patients having liver glycogen storage diseases, including Hers' disease (glycogen phosphorylase deficiency), display episodic hypoglycemia. These observations suggest that glycogenolysis may be a significant process for hepatic glucose production.

Glycogenolysis is catalyzed in liver, muscle, and brain by tissue-specific isoforms of the enzyme glycogen phosphorylase. This enzyme cleaves the glycogen macromolecule releasing glucose-1-phosphate and a new shortened glycogen macromolecule. Two types of glycogen phosphorylase inhibitors have been reported to date: glucose and glucose analogs [J. L. Martin, et al., Biochemistry, 30, 10101, (1991)], and caffeine and other purine analogs [P. J. Kasvinsky, et al., J. Biol. Chem., 253, 3343–3351 and 9102–9106 (1978)]. These compounds, and glycogen phosphorylase inhibitors in general, have been postulated to be of potential use for the treatment of Type 2 diabetes by decreasing hepatic glucose production and lowering glycemia. See, for example, T. B. Blundell, et al., Diabetologia, 35 (Suppl. 2), 569–576 (1992), and Martin et al., supra.

Recently, glycogen phosphorylase inhibitors have been disclosed in, inter alia, PCT International Application Publication No. WO 97/31901, and in commonly-assigned U.S. Pat. Nos. 6,107,329, 6,277,877, and 6,297,269. The commonly-assigned U.S. Pat. Nos. 6,107,329, 6,277,877, and 6,297,269, the disclosures of which are incorporated herein by reference in their entirety, disclose novel substituted N-(indole-2-carbonyl)-β-alaninamide compounds, including 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, denoted hereinbelow as the compound of Formula (I); certain derivatives thereof; processes for the production thereof; pharmaceutical compositions comprising such compounds or such derivatives; and methods of treating glycogen phosphorylase dependent diseases or conditions by administering such compounds, such pharmaceutical compositions, or such derivatives, to a mammal in need of such treatment.

The present invention relates to crystal forms of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide; processes for the production thereof, pharmaceutical compositions comprising such polymorphs; and uses thereof.

SUMMARY OF THE INVENTION

The instant invention provides crystal forms of 5-chloro-N-[(1S,2R)-3-[3R,4S]-4-dihydroxy-1-pyrrolidinyl]-2-hydroxy-3-oxo-1-(phenylmethyl)propyl]-1H-indole-2-carboxamide (I)

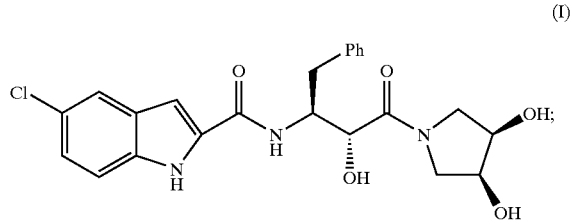

(I)

processes for the production of such forms; pharmaceutical compositions comprising such forms; and methods of treating glycogen phosphorylase dependent diseases, or conditions with such crystal forms, or such pharmaceutical compositions.

DETAILED DESCRIPTION OF THE INVENTION

The invention provides crystal forms of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, depicted hereinbelow as the compound of Formula (I).

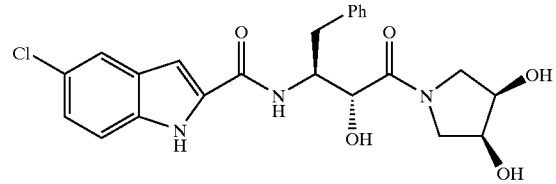

(I)

As employed throughout the instant description and appendant claims, the term "crystal forms of the instant invention" means, as appropriate, a crystal form of 5-chloro-N-[(1S,2R)-3-(3R,4S]-3,4-dihydroxy-1-pyrrolidinyl]-2-hydroxy-3-oxo-1-(phenylmethyl)propyl]-1H-indole-2-carboxamide, designated Form A, Form B, Form C, Form D, Form E, Form F, and/or Form G as defined hereinbelow.

The crystal forms of the instant invention have been characterized using X-ray diffractometry. One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffractiorf angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

In one aspect, the invention provides amorphous 5-chloro-N-[(1S,2R)-3-(3R,4S]-3,4-dihydroxy-1-pyrrolidinyl]-2-hydroxy-3-oxo-1-(phenylmethyl)propyl]-1H-indole-2-carboxamide.

Figure 1:
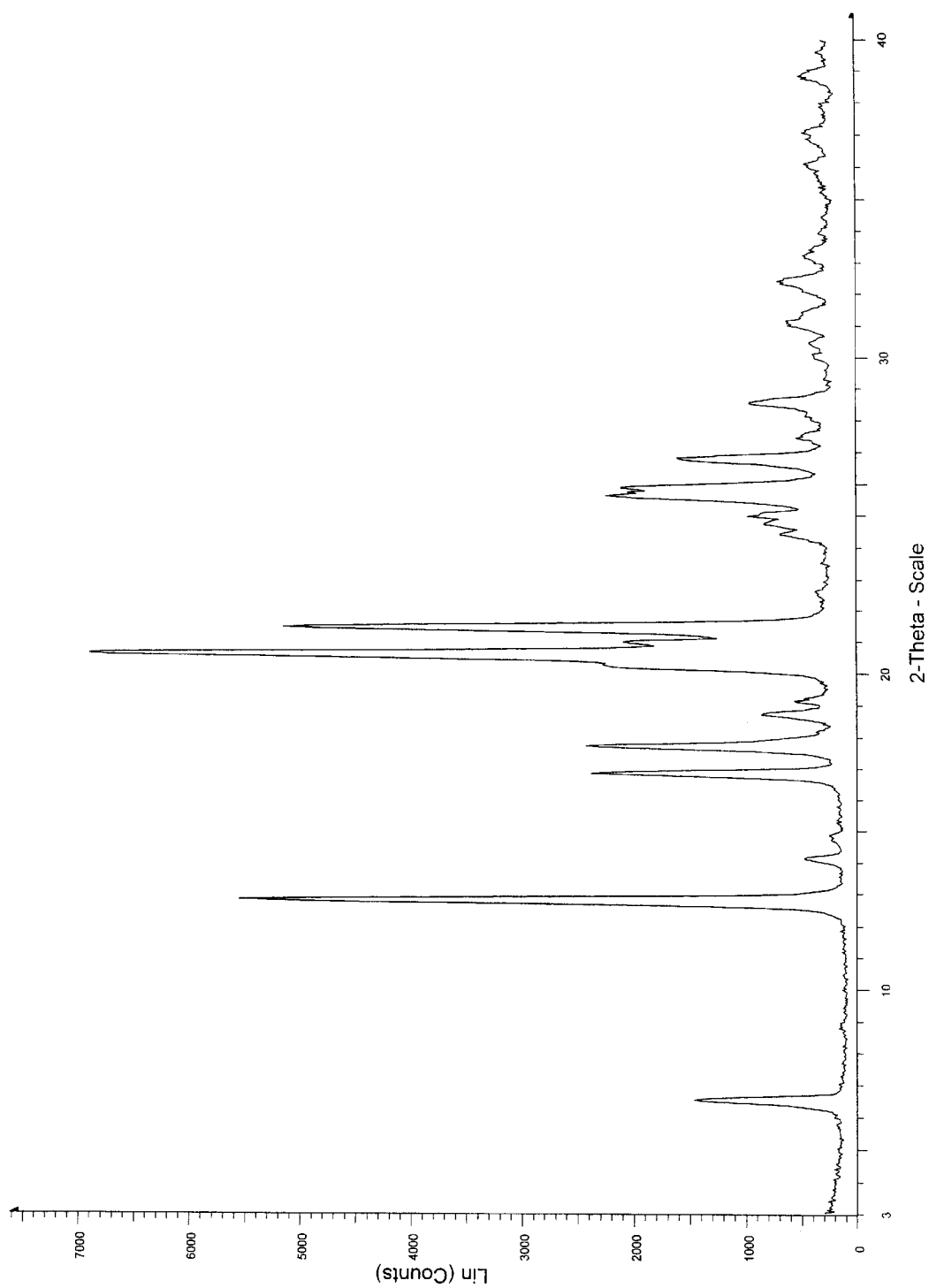
FIG. 1 is a characteristic X-ray diffraction pattern illustrating that the crystal form, designated hereinbelow as Form A, of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, is crystalline.

In another aspect of the invention, there is provided a crystal form of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, designated hereinafter as Form A, which crystal form exhibits an X-ray diffraction pattern substantially identical to that depicted in FIG. 1, having characteristic high intensity peaks, expressed in degrees 2-theta, of about 12.73, 16.82, 17.67, 20.24, 20.56, 20.96, 21.41, 25.61 and 25.85, and X-ray diffraction d-spacings, expressed in Å, of about 6.95, 5.27, 5.02, 4.38, 4.32, 4.23, 4.15, 3.48, and 3.44, respectively. The invention also provides a Form A crystal form that exhibits an X-ray diffraction pattern substantially the same as that depicted in FIG. 1, having characteristic diffraction peaks expressed in degrees 2-theta, diffraction d-spacings expressed in Å, and intensities (I), at approximately the values shown in Table 1 hereinbelow.

TABLE 1

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide
Form A

| Angle 2-Theta | d-value (Å) | I |
| --- | --- | --- |
| 6.48 | 13.62 | 20.9 |
| 12.73 | 6.95 | 80.4 |
| 14.11 | 6.27 | 6.7 |
| 16.82 | 5.27 | 34.4 |
| 17.67 | 5.02 | 35.0 |
| 18.69 | 4.74 | 12.3 |
| 19.12 | 4.64 | 8.0 |
| 20.24 | 4.38 | 32.8 |
| 20.56 | 4.32 | 100.0 |
| 20.96 | 4.23 | 30.1 |
| 21.41 | 4.15 | 74.7 |
| 22.54 | 3.94 | 5.2 |
| 24.44 | 3.64 | 9.8 |
| 24.72 | 3.60 | 11.9 |
| 25.01 | 3.56 | 14.0 |
| 25.61 | 3.48 | 32.4 |
| 25.85 | 3.44 | 30.4 |
| 26.76 | 3.33 | 23.2 |
| 27.47 | 3.24 | 7.7 |
| 28.08 | 3.18 | 6.5 |
| 28.55 | 3.12 | 13.8 |
| 30.04 | 2.97 | 5.3 |
| 30.46 | 2.93 | 6.0 |
| 31.10 | 2.87 | 8.9 |
| 31.44 | 2.84 | 6.9 |
| 32.39 | 2.76 | 10.1 |
| 33.24 | 2.69 | 6.7 |
| 35.76 | 2.51 | 5.0 |
| 36.09 | 2.49 | 6.6 |
| 36.87 | 2.44 | 6.2 |
| 37.12 | 2.42 | 6.8 |
| 38.85 | 2.32 | 7.3 |

In another aspect, the invention provides a crystal form of anhydrous 5-chloro-N-[(1S,2R)-3-[3R,4S]-3,4-dihydroxy-1-pyrrolidinyl]-2-hydroxy-3-oxo-1-(phenylmethyl)propyl]-

Figure 2:
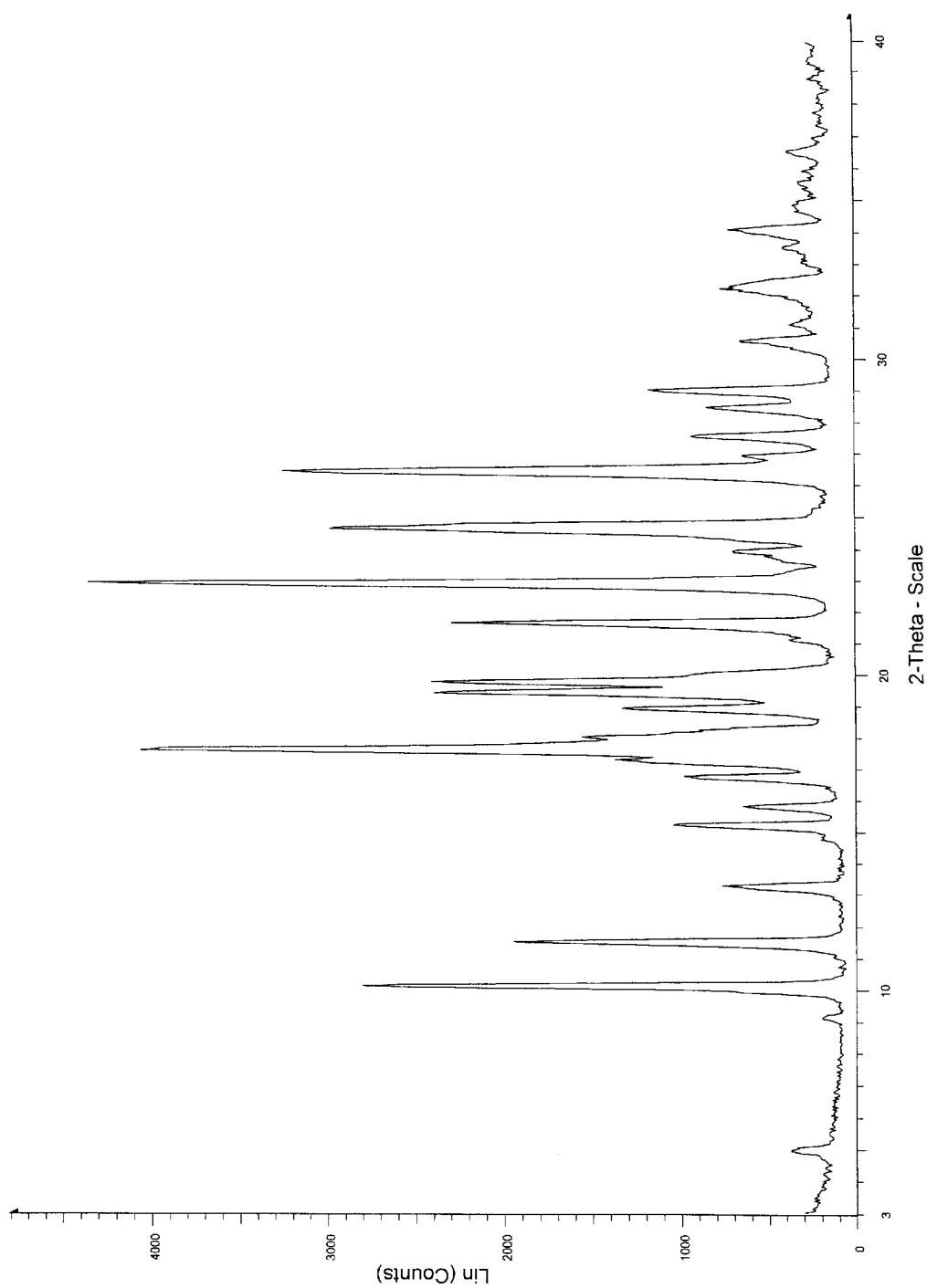
FIG. 2 is a characteristic X-ray diffraction pattern illustrating that the crystal form, designated hereinbelow as Form B, of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, is crystalline.

1H-indole-2-carboxamide, designated hereinafter as Form B, which crystal form exhibits an X-ray diffraction pattern substantially identical to that depicted in FIG. 2, having characteristic high intensity peaks, expressed in degrees 2-theta, of about 10.08, 11.49, 17.59, 19.42, 19.75, 21.65, 22.91, 24.66 and 26.42, and X-ray diffraction d-spacings, expressed in Å, of about 8.77, 7.70, 5.04, 4.57, 4.49, 4.10, 3.88, 3.61, and 3.37, respectively. The invention also provides a Form B crystal form that exhibits an X-ray diffraction pattern substantially the same as that depicted in FIG. 2, having characteristic diffraction peaks expressed in degrees 2-theta, diffraction d-spacings expressed in Å, and intensities (I), at approximately the values shown in Table 2 hereinbelow.

TABLE 2

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide
Form B

| Angle 2-Theta | d-value (Å) | I |
|---|---|---|
| 3.45 | 25.61 | 5.4 |
| 4.93 | 17.91 | 8.4 |
| 10.08 | 8.77 | 64.1 |
| 11.49 | 7.70 | 44.4 |
| 13.22 | 6.69 | 17.3 |
| 15.21 | 5.82 | 23.7 |
| 15.79 | 5.61 | 14.6 |
| 16.75 | 5.29 | 22.3 |
| 17.27 | 5.13 | 31.2 |
| 17.59 | 5.04 | 93.2 |
| 18.00 | 4.92 | 35.5 |
| 18.28 | 4.85 | 20.4 |
| 18.91 | 4.69 | 30.2 |
| 19.42 | 4.57 | 54.7 |
| 19.75 | 4.49 | 55.1 |
| 20.08 | 4.42 | 20.1 |
| 21.15 | 4.20 | 8.4 |
| 21.65 | 4.10 | 52.5 |
| 22.91 | 3.88 | 100.0 |
| 23.72 | 3.75 | 10.7 |
| 23.95 | 3.71 | 15.8 |
| 24.66 | 3.61 | 68.4 |
| 26.42 | 3.37 | 74.6 |
| 26.93 | 3.31 | 14.5 |
| 27.58 | 3.23 | 21.2 |
| 28.46 | 3.13 | 19.2 |
| 29.02 | 3.07 | 26.8 |
| 30.61 | 2.92 | 14.8 |
| 31.13 | 2.87 | 8.3 |
| 32.27 | 2.77 | 17.4 |

TABLE 2-continued

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide
Form B

| Angle 2-Theta | d-value (Å) | I |
|---|---|---|
| 33.10 | 2.70 | 6.7 |
| 33.60 | 2.67 | 9.1 |
| 34.10 | 2.63 | 16.3 |
| 34.90 | 2.57 | 7.8 |
| 35.56 | 2.52 | 6.9 |
| 35.95 | 2.50 | 6.5 |
| 36.55 | 2.46 | 8.5 |
| 36.96 | 2.43 | 5.2 |
| 37.78 | 2.38 | 5.0 |
| 38.88 | 2.31 | 5.7 |
| 39.40 | 2.29 | 5.8 |

Figure 3:
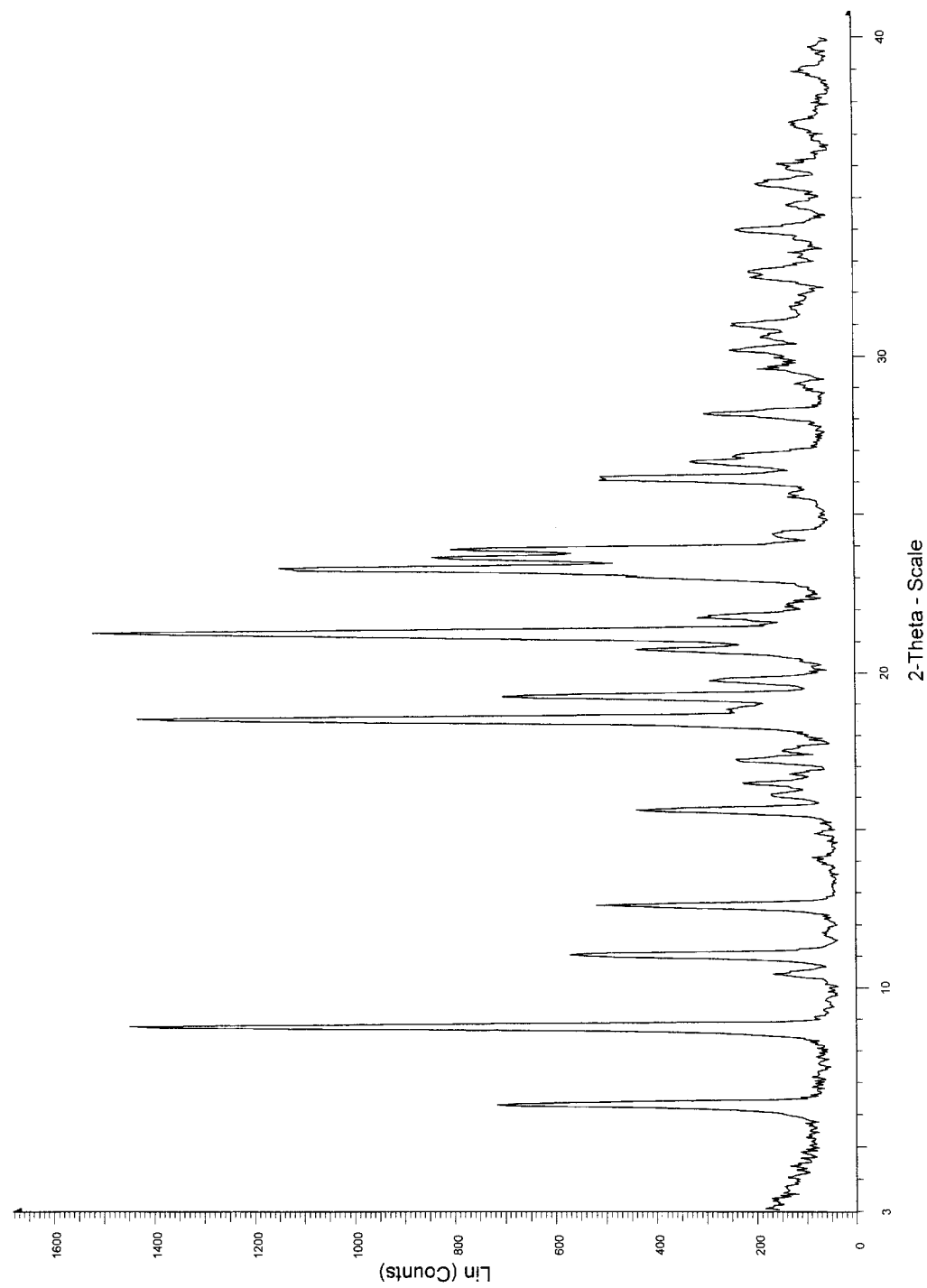
FIG. 3 is a characteristic X-ray diffraction pattern illustrating that the crystal form, designated hereinbelow as Form C, of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, mono-ethanolate, is crystalline.

In yet another aspect, the invention provides a crystal form of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, mono-ethanolate, designated hereinafter as Form C, and depicted hereinbelow as the compound of Formula (II), which crystal form exhibits an X-ray diffraction pattern substantially identical to that depicted in FIG. 3, having characteristic high intensity peaks, expressed in degrees 2-theta, of about 6.26, 8.70, 18.46, 19.22, 21.24, 23.27, 23.62, 23.87, and X-ray diffraction d-spacings, expressed in Å, of about 14.12, 10.16, 4.80, 4.61, 4.18, 3.82, 3.76, and 3.72, respectively. The invention also provides a Form C crystal form that exhibits an X-ray diffraction pattern substantially the same as that depicted in FIG. 3, having characteristic diffraction peaks expressed in degrees 2-theta, diffraction d-spacings expressed in Å, and intensities (I), at approximately the values shown in Table 3 hereinbelow.

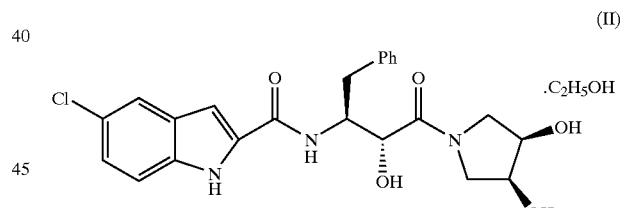

(II)

TABLE 3

5-Chloro-N-[(1S,2R)-3-[3R,4S,]-3,4-dihydroxy-1-pyrrolidinyl]-2-hydroxy-3-oxo-1-(phenylmethyl)propyl]-1H-indole-2-carboxamide, mono-thanolate
Form C

| Angle 2-Theta | d-value (Å) | I | Angle 2-Theta | d-value (Å) | I | Angle 2-Theta | d-value (Å) | I |
|---|---|---|---|---|---|---|---|---|
| 4.36 | 20.25 | 8.6 | 19.75 | 4.49 | 18.9 | 29.13 | 3.06 | 7.5 |
| 6.26 | 14.12 | 46.8 | 20.71 | 4.28 | 28.6 | 29.63 | 3.01 | 12.4 |
| 8.70 | 10.16 | 95.0 | 21.24 | 4.18 | 100.0 | 30.23 | 2.95 | 16.0 |
| 10.40 | 8.50 | 10.7 | 21.77 | 4.08 | 20.5 | 30.61 | 2.92 | 12.0 |
| 10.99 | 8.05 | 37.3 | 22.14 | 4.01 | 9.0 | 31.00 | 2.88 | 15.8 |
| 12.56 | 7.04 | 33.8 | 23.27 | 3.82 | 75.5 | 32.49 | 2.75 | 13.3 |
| 15.57 | 5.69 | 28.6 | 23.62 | 3.76 | 55.3 | 33.26 | 2.69 | 8.2 |
| 16.06 | 5.52 | 10.9 | 23.87 | 3.72 | 52.8 | 33.98 | 2.64 | 15.2 |
| 16.41 | 5.40 | 14.6 | 24.33 | 3.65 | 10.5 | 34.78 | 2.58 | 8.5 |
| 16.76 | 5.29 | 8.5 | 25.61 | 3.48 | 8.4 | 35.46 | 2.53 | 12.6 |

TABLE 3-continued

5-Chloro-N-[(1S,2R)-3-[3R,4S,]-3,4-dihydroxy-1-pyrrolidinyl]-2-hydroxy-3-oxo-1-(phenylmethyl)propyl]-1H-indole-2-carboxamide, mono-thanolate
Form C

| Angle 2-Theta | d-value (Å) | I | Angle 2-Theta | d-value (Å) | I | Angle 2-Theta | d-value (Å) | I |
|---|---|---|---|---|---|---|---|---|
| 17.18 | 5.16 | 15.5 | 26.10 | 3.41 | 33.1 | 36.00 | 2.49 | 8.8 |
| 17.49 | 5.07 | 9.4 | 26.60 | 3.35 | 21.3 | 37.36 | 2.40 | 8.0 |
| 18.46 | 4.80 | 94.1 | 26.88 | 3.31 | 15.4 | 39.03 | 2.31 | 6.7 |
| 19.22 | 4.61 | 46.1 | 28.16 | 3.17 | 19.4 | | | |

Figure 4:
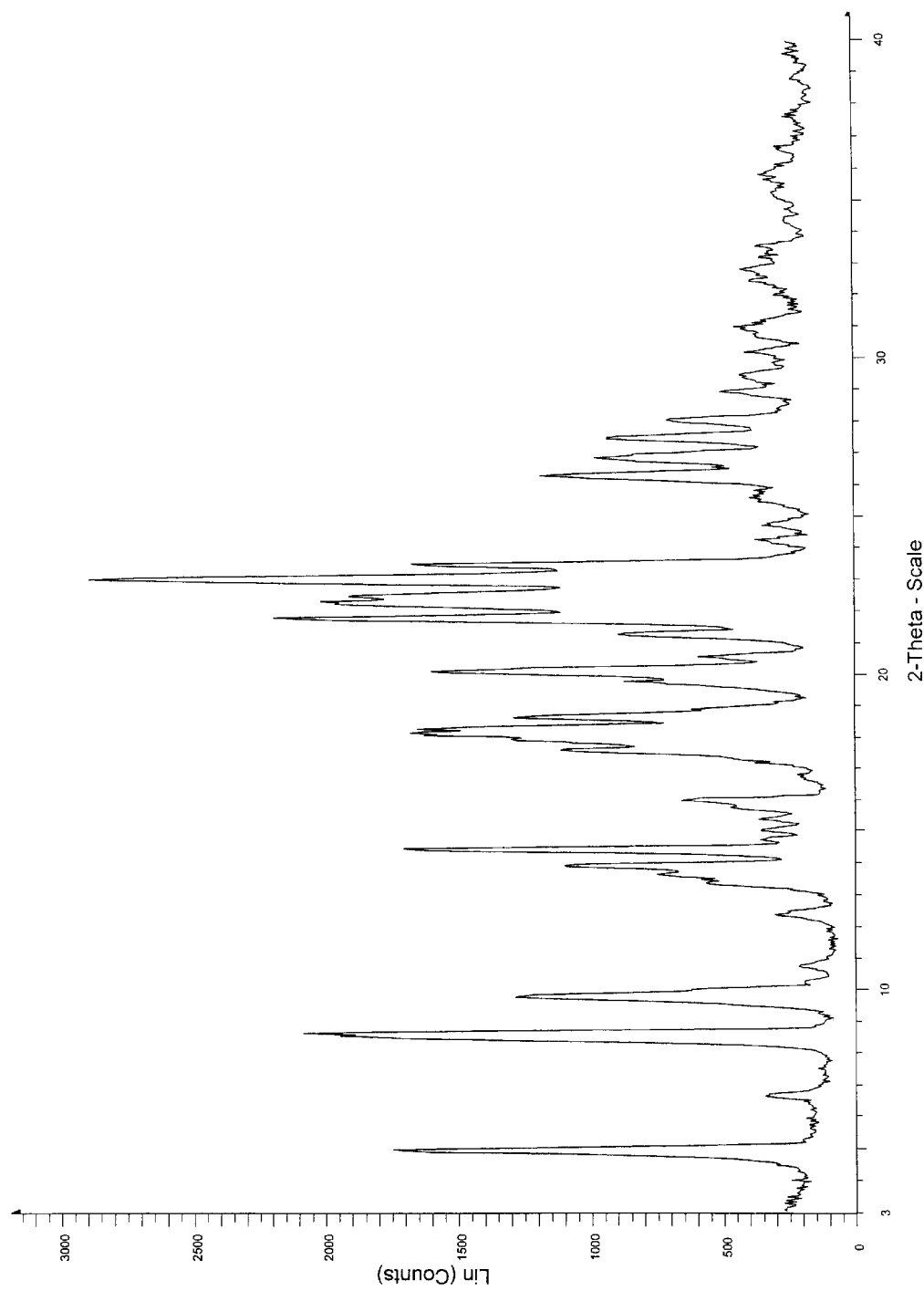
FIG. 4 is a characteristic X-ray diffraction pattern illustrating that the crystal form, designated hereinbelow as Form D, of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, dihydrate, is crystalline.

In yet another aspect, the present invention provides a crystal form of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, dihydrate, designated hereinafter as Form D, and depicted hereinbelow as the compound of Formula (III), which crystal form exhibits an X-ray diffraction pattern substantially identical to that depicted in FIG. 4, having characteristic high intensity peaks, expressed in degrees 2-theta, of about 4.90, 8.53, 14.38, 18.13, 21.74, 22.23, 22.46, 22.97 and 23.45, and X-ray diffraction d-spacings, expressed in Å, of about 18.02, 10.36, 6.15, 4.89, 4.08, 4.00, 3.96, 3.87, and 3.79, respectively. The invention also provides a Form D crystal form that exhibits an X-ray diffraction pattern substantially the same as that depicted in FIG. 4, having characteristic diffraction peaks expressed in degrees 2-theta, diffraction d-spacings expressed in Å, and intensities (I), at approximately the values shown in Table 4 hereinbelow.

Figure 5:
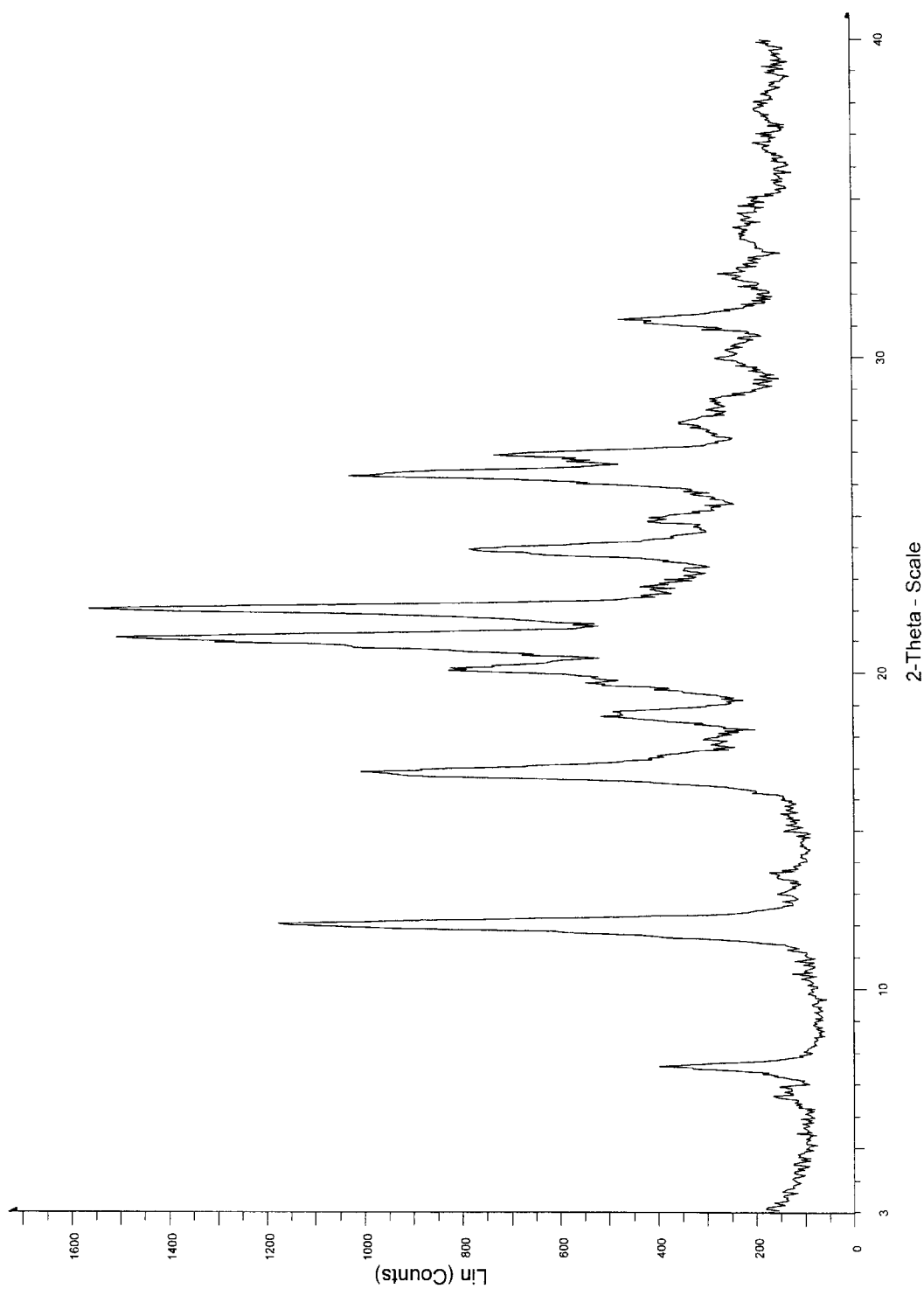
FIG. 5 is a characteristic X-ray diffraction pattern illustrating that the crystal form, designated hereinbelow as Form E, of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, hemi-ethanolate, is crystalline.

In yet another aspect, the instant invention provides a crystal form of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, hemi-ethanolate, designated hereinafter as Form E, and depicted hereinbelow as the compound of Formula (IV), which crystal form exhibits an X-ray diffraction pattern substantially identical to that depicted in FIG. 5, having characteristic high intensity peaks, expressed in degrees 2-theta, of about 11.97, 16.80, 20.07, 21.06, 22.00, 23.89, and 26.27, and X-ray diffraction d-spacings, expressed in Å, of about 7.39, 5.27, 4.42, 4.22, 4.04, 3.72, and 3.39, respectively. The invention also provides a Form E crystal form that exhibits an X-ray diffraction pattern substantially the same as that depicted in FIG. 5, having characteristic diffraction peaks expressed in degrees 2-theta, diffraction d-spacings expressed in Å, and intensities (I), at approximately the values shown in Table 5 hereinbelow.

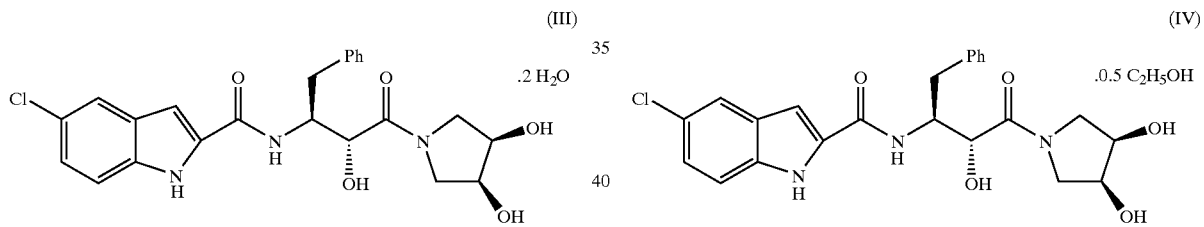

TABLE 4

5-Chloro-N-[(1S,2R)-3-[3R,4S,]-3,4-dihydroxy-1-pyrrolidinyl]-2-hydroxy-3-oxo-1-(phenylmethyl)propyl]-1H-indole-2-carboxamide, dihydrate
Form D

| Angle 2-Theta | d-value (Å) | I | Angle 2-Theta | d-value (Å) | I | Angle 2-Theta | d-value (Å) | I |
|---|---|---|---|---|---|---|---|---|
| 4.90 | 18.02 | 60.1 | 18.61 | 4.76 | 44.4 | 27.46 | 3.24 | 32.0 |
| 6.61 | 13.35 | 11.6 | 19.74 | 4.49 | 29.9 | 28.04 | 3.18 | 24.2 |
| 8.53 | 10.36 | 71.8 | 20.08 | 4.42 | 55.1 | 28.94 | 3.08 | 17.2 |
| 9.75 | 9.07 | 44.2 | 20.56 | 4.32 | 20.2 | 29.46 | 3.03 | 14.6 |
| 13.32 | 6.64 | 19.3 | 21.26 | 4.18 | 30.7 | 30.23 | 2.95 | 14.0 |
| 13.64 | 6.49 | 25.7 | 21.74 | 4.08 | 75.7 | 30.70 | 2.91 | 12.5 |
| 13.86 | 6.39 | 37.8 | 22.23 | 4.00 | 69.6 | 30.94 | 2.89 | 15.3 |
| 14.38 | 6.15 | 58.7 | 22.46 | 3.96 | 65.9 | 31.24 | 2.86 | 11.8 |
| 14.72 | 6.01 | 12.1 | 22.97 | 3.87 | 100.0 | 32.03 | 2.79 | 10.1 |
| 14.98 | 5.91 | 12.1 | 23.45 | 3.79 | 57.7 | 32.48 | 2.75 | 13.3 |
| 15.32 | 5.78 | 12.4 | 24.22 | 3.67 | 12.7 | 32.83 | 2.73 | 14.4 |
| 15.76 | 5.62 | 16.1 | 24.72 | 3.60 | 11.8 | 33.57 | 2.67 | 12.5 |
| 15.96 | 5.55 | 22.5 | 25.63 | 3.47 | 13.3 | 35.23 | 2.55 | 10.4 |
| 17.55 | 5.05 | 38.2 | 26.28 | 3.39 | 40.8 | 35.72 | 2.51 | 11.4 |
| 18.13 | 4.89 | 57.8 | 26.83 | 3.32 | 33.7 | | | |

TABLE 5

5-Chloro-N-[(1S,2R)-3-[3R,4S,]-3,4-dihydroxy-1-pyrrolidinyl]-2-hydroxy-3-oxo-1-(phenylmethyl)propyl]-1H-indole-2-carboxamide, hemi-ethanolate
Form E

| Angle 2-Theta | d-value (Å) | I | Angle 2-Theta | d-value (Å) | I | Angle 2-Theta | d-value (Å) | I |
|---|---|---|---|---|---|---|---|---|
| 4.75 | 18.60 | 7.2 | 17.88 | 4.96 | 19.5 | 26.90 | 3.31 | 46.8 |
| 6.57 | 13.45 | 10.4 | 18.65 | 4.75 | 32.7 | 27.97 | 3.19 | 22.5 |
| 6.82 | 12.94 | 9.5 | 19.62 | 4.52 | 34.7 | 28.66 | 3.11 | 18.4 |
| 7.53 | 11.74 | 25.2 | 20.07 | 4.42 | 52.8 | 29.98 | 2.98 | 17.8 |
| 9.81 | 9.01 | 5.8 | 21.06 | 4.22 | 96.4 | 31.19 | 2.87 | 30.3 |
| 10.47 | 8.44 | 7.8 | 22.00 | 4.04 | 100.0 | 32.60 | 2.74 | 17.4 |
| 11.97 | 739 | 75.1 | 22.72 | 3.91 | 27.7 | 36.72 | 2.45 | 12.7 |
| 13.00 | 6.80 | 9.8 | 23.89 | 3.72 | 50.1 | 37.03 | 2.43 | 12.2 |
| 13.54 | 6.54 | 9.9 | 24.86 | 3.58 | 26.6 | | | |
| 16.80 | 5.27 | 64.3 | 26.27 | 3.39 | 65.9 | | | |

Figure 6:
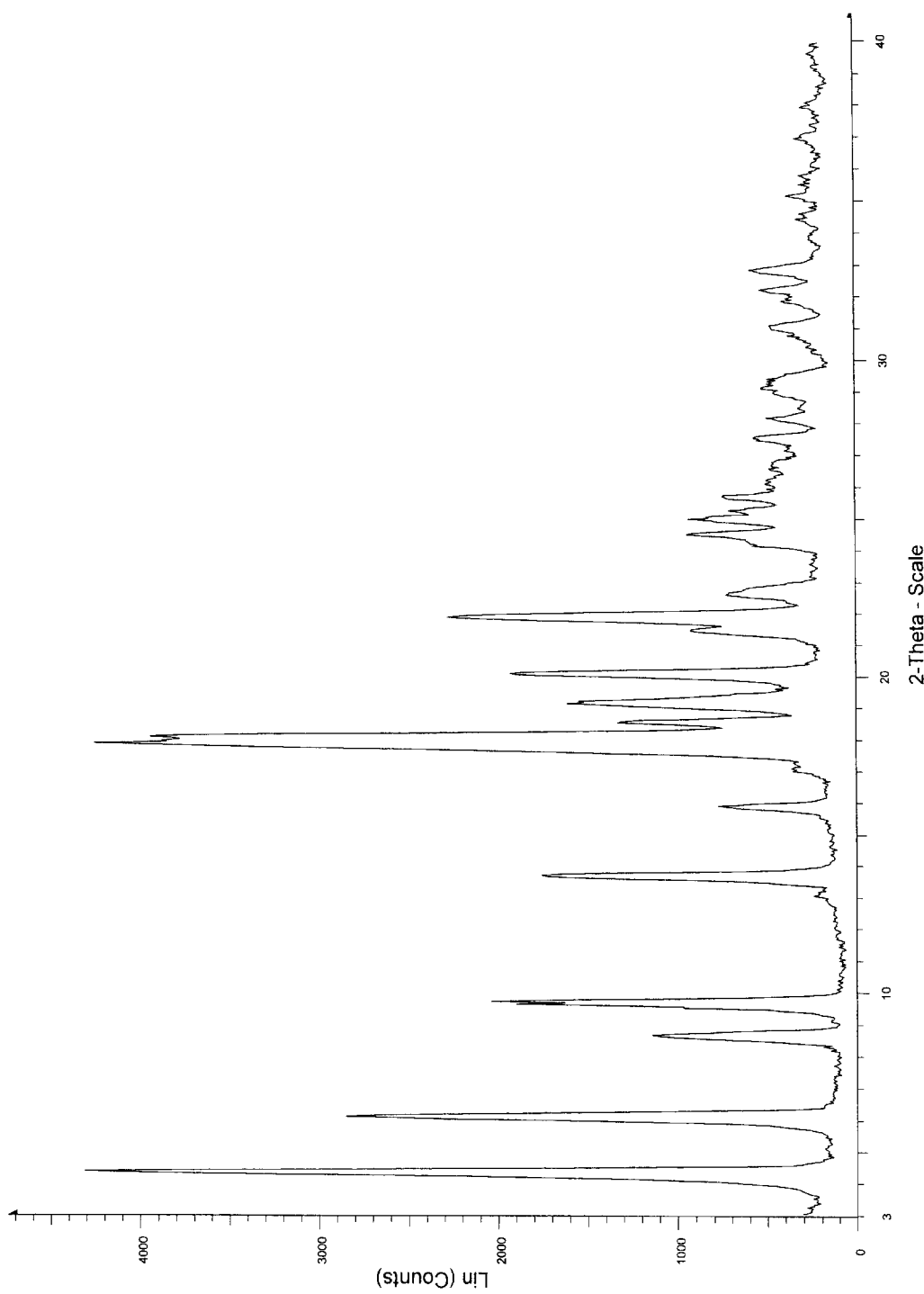
FIG. 6 is a characteristic X-ray diffraction pattern illustrating that the crystal form, designated hereinbelow as Form F, of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, monohydrate, is crystalline.

In yet another aspect, the invention provides a crystal form of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, monohydrate, designated hereinafter as Form F, and depicted hereinbelow as the compound of Formula (V), which crystal form exhibits an X-ray diffraction pattern substantially identical to that depicted in FIG. 6, having characteristic high intensity peaks, expressed in degrees 2-theta, of about 4.30, 6.07, 9.67, 13.66, 17.88, 20.09, and 21.88, and X-ray diffraction d-spacings, expressed in Å, of about 20.54, 14.54, 9.14, 6.48, 4.96, 4.42,

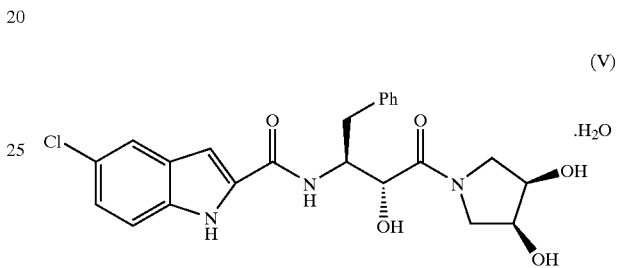

(V)

TABLE 6

5-Chloro-N-[(1S,2R)-3-[3R,4S,]-3,4-dihydroxy-1-pyrrolidinyl]-2-hydroxy-3-oxo-1-(phenylmethyl)propyl]-1H-indole-2-carboxamide, monohydrate
Form F

| Angle 2-Theta | d-value (Å) | I | Angle 2-Theta | d-value (Å) | I | Angle 2-Theta | d-value (Å) | I |
|---|---|---|---|---|---|---|---|---|
| 4.30 | 20.54 | 100.0 | 22.62 | 3.93 | 16.7 | 31.07 | 2.88 | 10.9 |
| 6.07 | 14.54 | 66.1 | 24.28 | 3.66 | 14.0 | 31.92 | 2.80 | 9.3 |
| 8.61 | 10.26 | 26.3 | 24.54 | 3.62 | 21.8 | 32.25 | 2.77 | 12.2 |
| 9.67 | 9.14 | 47.2 | 25.03 | 3.56 | 21.6 | 32.86 | 2.72 | 13.5 |
| 13.09 | 6.76 | 5.4 | 25.32 | 3.51 | 16.3 | 33.88 | 2.64 | 5.8 |
| 13.66 | 6.48 | 40.6 | 25.69 | 3.46 | 17.1 | 34.61 | 2.59 | 6.9 |
| 15.86 | 5.58 | 17.8 | 26.20 | 3.40 | 11.4 | 35.19 | 2.55 | 8.6 |
| 17.04 | 5.20 | 8.2 | 26.63 | 3.34 | 11.0 | 35.81 | 2.51 | 7.0 |
| 17.88 | 4.96 | 98.9 | 27.55 | 3.23 | 13.0 | 36.20 | 2.48 | 5.3 |
| 18.54 | 4.78 | 30.7 | 28.18 | 3.16 | 11.4 | 37.03 | 2.43 | 7.5 |
| 19.14 | 4.63 | 37.3 | 29.00 | 3.08 | 10.4 | 37.98 | 2.37 | 6.8 |
| 20.09 | 4.42 | 44.7 | 29.16 | 3.06 | 12.0 | 39.24 | 2.29 | 5.2 |
| 21.47 | 4.14 | 21.3 | 29.40 | 3.04 | 11.3 | 39.69 | 2.27 | 5.8 |
| 21.88 | 4.06 | 53.0 | 30.36 | 2.94 | 5.5 | | | | and 4.06, respectively. The invention also provides a Form F crystal form that exhibits an X-ray diffraction pattern substantially the same as that depicted in FIG. 6, having characteristic diffraction peaks expressed in degrees 2-theta, diffraction d-spacings expressed in Å, and intensities (I), at approximately the values shown in Table 6 hereinbelow.

Figure 7:
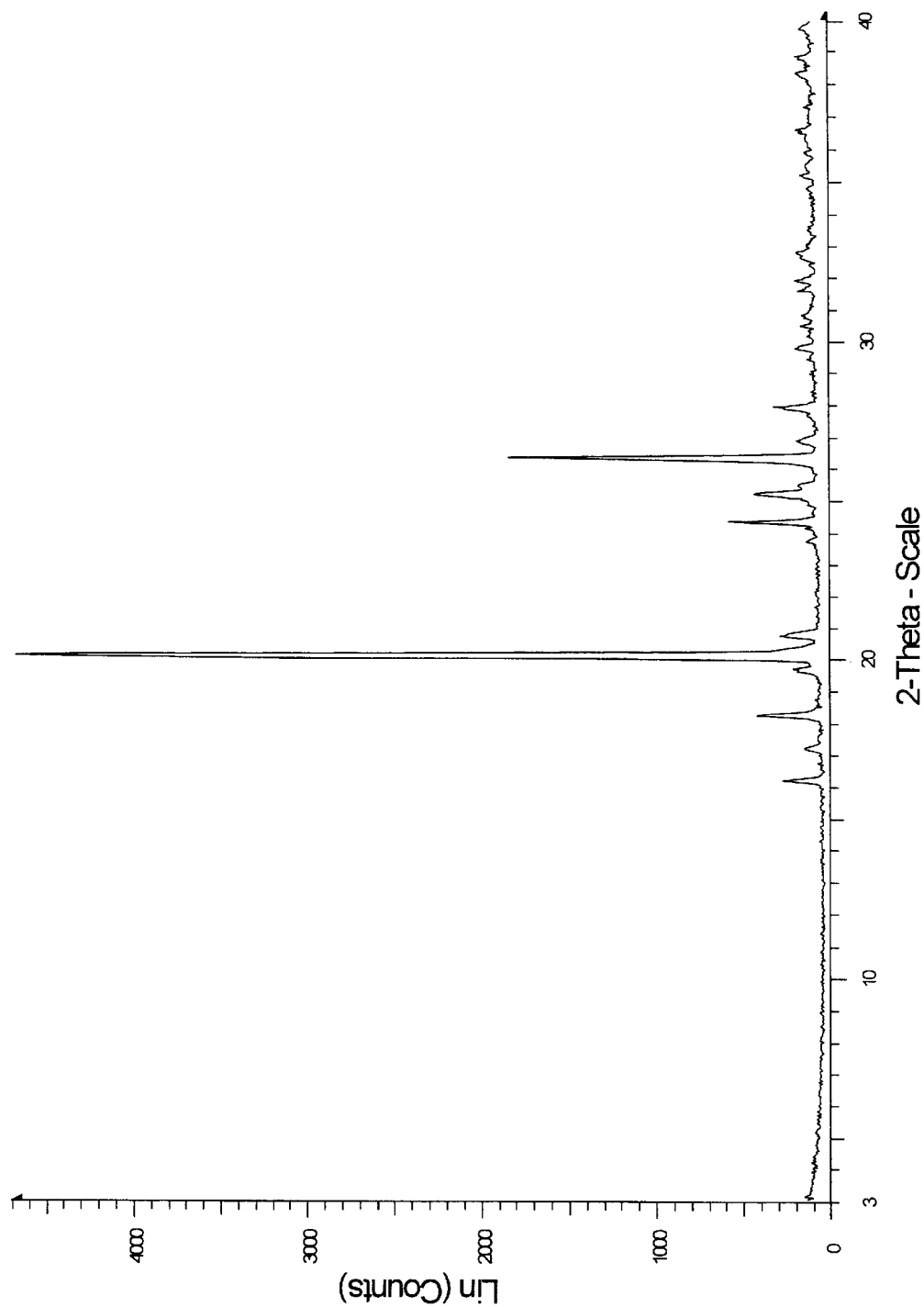
FIG. 7 is a characteristic X-ray diffraction pattern illustrating that the crystal form, designated hereinbelow as Form G, of anhydrous 5-chloro-N-[(1S,2R)-3-3R,4S]-3,4-dihydroxy-1-pyrrolidinyl]-2-hydroxy-3-oxo-1-(phenylmethyl)propyl]-1H-indole-2-carboxamide, is crystalline.

In yet another aspect, the invention further provides a crystal form of anhydrous 5-chloro-N-[(1S,2R)-3-[3R,4S]-3,4-dihydroxy-1-pyrrolidinyl]-2-hydroxy-oxo-1-(phenylmethyl)propyl]-1H-indole-2-carboxamide, designated hereinafter as Form G, which crystal form exhibits an X-ray diffraction pattern substantially identical to that depicted in FIG. 7, having characteristic high intensity peaks, expressed in degrees 2-theta, of about 18.2, 20.1, 24.3, 25.2, and 26.3, and X-ray diffraction d-spacings, expressed in Å, of about 4.9, 4.4, 3.7, 3.5, and 3.4, respectively. The invention also provides a Form G crystal form that exhibits an X-ray diffraction pattern substantially the same as that depicted in FIG. 6, having characteristic diffraction peaks expressed in degrees 2-theta, diffraction d-spacings expressed in Å, and intensities (I), at approximately the values shown in Table 7 hereinbelow.

TABLE 7

5-Chloro-N-[(1S,2R)-3-[3R,4S]-3,4-dihydroxy-1-pyrrolidinyl]-
2-hydroxy-3-oxo-1-(phenylmethyl)propyl]-
1H-indole-2-carboxamide
Form G

| Angle 2-Theta | d-value (Å) | I |
| --- | --- | --- |
| 16.2 | 5.5 | 5.4 |
| 17.2 | 5.1 | 2.8 |
| 18.2 | 4.9 | 8.6 |
| 19.7 | 4.5 | 4.1 |
| 20.1 | 4.4 | 100.0 |
| 20.8 | 4.3 | 5.8 |
| 23.7 | 3.7 | 2.5 |
| 24.3 | 3.7 | 12.1 |
| 25.2 | 3.5 | 8.9 |
| 26.3 | 3.4 | 38.6 |
| 26.9 | 3.3 | 3.6 |
| 27.9 | 3.2 | 6.4 |
| 29.4 | 3.0 | 2.3 |
| 29.8 | 3.0 | 3.9 |
| 30.8 | 2.9 | 2.9 |
| 31.6 | 2.8 | 3.5 |
| 31.9 | 2.8 | 3.8 |
| 32.7 | 2.7 | 3.7 |
| 34.8 | 2.6 | 2.4 |
| 35.2 | 2.5 | 3.2 |
| 35.5 | 2.5 | 2.7 |
| 35.9 | 2.5 | 2.7 |
| 36.6 | 2.4 | 3.6 |
| 38.4 | 2.3 | 3.7 |
| 38.8 | 2.3 | 3.3 |
| 39.8 | 2.3 | 3.1 |

In yet another aspect, the present invention provides a process for preparing the aforementioned anhydrous Form A crystal form, which process comprises azeotropically distilling a solution prepared from the 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, dihydrate (Form D) crystal form, in an aprotic solvent to substantially remove the water of hydration, and crystallize the Form A crystal form.

The solution prepared from the 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, dihydrate (Form D) crystal form, is prepared by suspending such crystal form in a suitable aprotic solvent, and stirring the suspension until dissolution is essentially complete. Preferred aprotic solvents useful in the instant process are those solvents selected from the group consisting of ethyl acetate, tetrahydrofuran, and mixtures of ethyl acetate and non-polar, ethyl acetate-miscible co-solvents, such as ethyl acetate/toluene. The use of ethyl acetate is particularly preferred.

The solution so prepared is then heated to a temperature, and for a time period, sufficient to substantially azeotropically remove the water of hydration and crystallize the Form A polymorph. The temperature typically employed in azeotropically dehydrating the Form D crystal form, and crystallizing the Form A crystal form, is normally the reflux temperature of the particular solvent employed. Such heating is typically conducted for a time period of between about one hour to about 24 hours, preferably about 8 hours. One of ordinary skill in the art will understand that the azeotropic removal of water from solvent mixtures may be quantified according to well-known methods, for example, through the use of a Dean-Stark apparatus, or similar means. The Form A crystal form so produced is then preferably isolated according to conventional techniques well-known to one of ordinary skill in the art, for example, by filtration.

Alternatively, the aforementioned anhydrous Form A crystal form may be prepared from the Form C crystal form as disclosed in Example 1a hereinbelow.

In yet another aspect, the present invention provides a process for preparing the aforementioned anhydrous Form B crystal form, which process comprises the steps of:

(a) adding water to a suspension of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form A), or 5-chloro-N-[(1S,2R)-3-[3R,4S]-3,4-dihydroxy-1-pyrrolidinyl]-2-hydroxy-3-oxo-1-(phenylmethyl)propyl)-1H-indole-2-carboxamide, dihydrate (Form D) crystal forms, in an aprotic solvent such that a water content of between about 0.5% and about 5.0% is achieved, and the Form A or the Form D crystal form is substantially dissolved to form a solution; and (b) allowing the Form B crystal form to crystallize from the solution.

The suspension of the anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form A), or 5-chloro-N-[(1S,2R)-3-[3R,4S]-3,4dihydroxy-1-pyrrolidinyl]-2-hydroxy-3-oxo-1-(phenylmethyl)propyl]-1H-indole-2-carboxamide, dihydrate (Form D) crystal forms is prepared by admixing either the Form A or the Form D crystal form in a suitable aprotic solvent with stirring. Preferred solvents useful in the instant process are those solvents selected from the group consisting of ethyl acetate, tetrahydrofuran, and mixtures of ethyl acetate and non-polar, ethyl acetate-miscible co-solvents, such as ethyl acetate/toluene. The use of ethyl acetate is particularly preferred.

The suspension of the Form A or Form D crystal form is then treated with water until a water content of between about 0.5% and about 5.0% has been achieved, and the Form A or Form D crystal form has been substantially dissolved. A water content of between about 1% and about 5% is generally preferred. Once the aforementioned water content has been achieved, the solution is filtered, if necessary to remove any trace insolubles that may be present, and then the Form B crystal form is allowed to crystallize therefrom.

Although the aqueous solution so prepared from either the Form A or Form D crystal form will normally precipitate the desired Form B crystal form upon prolonged standing, it is generally preferable to facilitate the crystallization process by heating the aqueous solution, preferably at the reflux temperature of the particular aprotic solvent employed with attendant agitation. The preferred reflux period may comprise from a few hours to one or more days, preferably from about eight to about 20 hours. The addition of Form B crystal form seed crystals to the aqueous solution prior to initiating reflux is typically preferred. Once crystallization of the desired Form B crystal form is essentially complete, excess water may be removed if desired, preferably by azeotropic distillation of the mixture at atmospheric pressure, and then the resulting suspension is cooled to between about 5° C. to about 30° C., preferably about room temperature, where the Form B crystal form so crystallized is then isolated by employing conventional techniques well-known to one of ordinary skill in the art, for example, by filtration.

In a further aspect of the invention, a process is provided wherein the anhydrous Form B crystal form so prepared may be purified, if desired, which process comprises the steps of:
(a) heating a suspension of the anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form B) crystal form in an aqueous solvent system comprising:
  (i) tetrahydrofuran and an aprotic, substantially tetrahydrofuran-miscible co-solvent; and
  (ii) about 3% to about 8% water; such that the Form B crystal form is substantially dissolved to form a solution; and
(b) heating the solution to substantially remove aqueous tetrahydrofuran and crystallize the Form B crystal form.

The suspension of the anhydrous 5-chloro-N-[(1S,2R)-3-(3R,4S]-3,4-dihydroxy-1-pyrrolidinyl]-2-hydroxy-3-oxo-1-(phenylmethyl)propyl]-1H-indole-2-carboxamide (Form B) crystal form is preferably prepared by suspending, with agitation, the compound in an aqueous solvent system. Generally preferred solvent systems useful in the instant process comprise about 1:1 (v/v) ratio mixtures of tetrahydrofuran and an aprotic, substantially tetrahydrofuran-miscible co-solvent, such as ethyl acetate. A solvent system comprising about a 1:1 (v/v) ratio ethyl acetate:tetrahydrofuran mixture is especially preferred. The suspension of the Form B crystal form so formed is then treated with water until a water content of between about 3% and about 8% has been achieved. A water content of between about 4% and about 5% is generally preferred.

Once the aforementioned water content has been achieved, the resulting suspension is heated to substantially dissolve the Form B crystal form and form a solution. This heating is subsequently maintained to substantially remove the tetrahydrofuran and crystallize the Form B crystal form. A temperature range of from about 70° C. to about 80° C. is generally preferred to substantially dissolve the Form B crystal form, substantially remove the tetrahydrofuran, and crystallize the Form B crystal form. Heating the solution at the reflux temperature of the solvent employed is especially preferred. A time period of from about three hours to about 72 hours is typically preferred. A time period of from about 12 to about 16 hours is especially preferred. The Form B crystal form so formed is then preferably isolated according to conventional techniques well-known to one of ordinary skill in the art, for example, by filtration.

In yet another aspect, the present invention provides a process for preparing the aforementioned Form D crystal form, which process comprises the steps of:
(a) adding water to a suspension of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form A), or anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form B) crystal forms in an aprotic solvent such that a water content of between about 5% and about 10% is achieved;
(b) heating the suspension to substantially dissolve the Form A or the Form B crystal form; and
(c) diluting the solution so formed with a non-polar, anti-solvent to crystallize the Form D crystal form.

The suspension of the anhydrous 5-chloro-N-[(1S,2R)-3-(3R,4S]-3,4-dihydroxy-1-pyrrolidinyl]-2-hydroxy-3-oxo-1-(phenylmethyl)propyl]-1H-indole-2-carboxamide (Form A), or anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form B) forms is prepared by admixing either compound with stirring in a suitable aprotic solvent. Preferred solvents useful in the instant process are those solvents selected from the group consisting of ethyl acetate, tetrahydrofuran, and mixtures of ethyl acetate and non-polar, ethyl acetate-miscible co-solvents, such as ethyl acetate/toluene. The use of ethyl acetate is particularly preferred.

The suspension prepared from the Form A or Form B crystal form is then treated with water until a water content of between about 5% and about 10% has been achieved. Once the aforementioned water content has been achieved, the solution is heated to a temperature of between about ambient temperature and about 50° C. for a time period sufficient to dissolve the Form A or Form B crystal form. A time period of from about one hour to about 72 hours is typically preferred. The solution is then diluted with a non-polar, anti-solvent to cause crystallization of the desired Form D crystal form. The term "non-polar, anti-solvent" denotes a non-polar organic solvent at least substantially miscible with the solvent employed to dissolve the Form A or Form B crystal form and which, upon admixture therewith, causes or induces crystallization of the Form D crystal form. Generally useful non-polar, anti-solvents that may be successfully employed in the dilution step are those anti-solvents selected from the group consisting of hexanes, heptanes, octane, and petroleum ether. The use of hexanes or heptanes is typically preferred. The Form D crystal form so crystallized is then preferably isolated according to conventional techniques well-known to one of ordinary skill in the art, for example, by filtration.

Alternatively, the aforementioned Form D crystal form may be prepared from the Form C crystal form as disclosed in Example 6a hereinbelow.

In yet another aspect, the present invention provides pharmaceutical compositions comprising a crystal form, or forms, of the instant invention, and a pharmaceutically acceptable carrier, vehicle, or diluent. Preferred crystal forms, useful in the practice of the pharmaceutical compositions of the present invention, comprise the anhydrous Form A and Form B crystal forms of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, and the Form D crystal form of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, dihydrate.

In yet another aspect, the present invention provides methods of treating glycogen phosphorylase dependent diseases or conditions which methods comprise administering to a mammal in need of such treatment a crystal form, or forms, of the instant invention, or a pharmaceutical composition comprising such crystal form, or forms. Preferably, the glycogen phosphorylase dependent diseases and conditions treatable according to the methods of the present invention are selected from the group consisting of hypercholesterolemia, hyperglycemia, hyperinsulinemia, hyperlipidemia, hypertension, atherosclerosis, diabetes, diabetic cardiomyopathy, infection, tissue ischemia, myocardial ischemia, and tumor growth. Preferred crystal forms of the instant invention, useful in the practice of the instant methods of treating glycogen phosphorylase dependent diseases or conditions, comprise the Form A and Form B crystal forms of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, and the Form D crystal form of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, dihydrate.

The crystal forms of the instant invention can be administered to a mammal in need of treatment therewith at dosage levels in the range of from about 0.005 to about 50 mg/kg per day, preferably from about 0.01 to about 25 mg/kg per day, and most preferably from about 0.1 to about 15 mg/kg per day. However, some variability in the general dosage range may be required depending upon the age and weight of the subject being treated, the intended route of administration, and the like. The determination of dosage ranges and optimal dosages for a particular patient is well within the ability of one of ordinary skill in the art having benefit of the instant disclosure.

According to the methods of the invention, the crystal forms of the instant invention are administered to a mammal in need of treatment therewith, preferably in the form of a pharmaceutical composition comprising a pharmaceutically acceptable carrier, vehicle, or diluent. Accordingly, such crystal forms can be administered to a mammal in any conventional oral, rectal, transdermal, parenteral, (e.g., intravenous, intramuscular, or subcutaneous), intracisternal, intravaginal, intraperitoneal, intravesical, local (e.g., powder, ointment, or drop), buccal, or nasal dosage form.

Compositions suitable for parenteral injection may comprise pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (e.g., propylene glycol, polyethylene glycol, glycerol, and the like), suitable mixtures thereof, vegetable oils e.g., olive oil), and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of these compositions can be effected with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be effected by the use of agents capable of delaying absorption, for example, aluminum monostearate, and gelatin.

Solid dosage forms for oral administration include capsules, tablets, powders, and granules. In such dosage forms, the crystal forms of the instant invention are admixed with at least one inert customary pharmaceutical excipient (or carrier) such as sodium citrate, or dicalcium phosphate, or (a) fillers or extenders; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f absorption accelerators, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain certain opacifying agents, and can be of such composition that they release the active compound or compounds in a delayed manner. Examples of embedding compositions that can also be employed are polymeric substances and waxes. The crystal forms of the instant invention can also be incorporated in micro-encapsulated form, if appropriate, with one or more of the above-mentioned excipients.

Liquid dosage forms for oral administration include pharmaceutically acceptable emulsions, solutions, suspensions, syrups, and elixirs. In addition to the crystal forms of the instant invention, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oil, in particular, cottonseed oil, groundnut oil, corn germ oil, castor oil, and sesame seed oil, glycerol, tetrahydrofurfuryl alcohol, polyethylene glycols, and fatty acid esters of sorbitan, or mixtures of these substances, and the like.

Besides such inert diluents, the compositions may also comprise adjuvants, such as wetting agents, emulsifying and suspending agents, sweetening, flavoring, and perfuming agents.

Suspensions of the crystal forms of the instant invention may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by admixing the crystal forms of the instant invention with suitable non-irritating excipients or carriers such as cocoa butter, polyethylene glycol, or a suppository wax, which are solid at normal room temperature, but liquid at body temperature and, therefore, melt in the rectum or vaginal cavity thereby releasing such crystal forms.

Dosage forms for topical administration may comprise ointments, powders, sprays, and inhalants. The crystal forms of the instant invention are admixed under sterile conditions with a pharmaceutically acceptable carrier, and any preservatives, buffers, or propellants that may also be required. Opthalmic formulations, eye ointments, powders, and solutions are also intended to be included within the scope of the present invention.

Experimental

The present invention is illustrated by the following Examples. It is to be understood, however, that the invention is not limited to the specific details of these examples, as other variations thereof will be known, or apparent in light of the instant disclosure, to one of ordinary skill in the art.

The X-ray diffraction patterns of the crystal forms of the instant invention, depicted in the accompanying Figures, were measured with a Siemens D5000 X-ray diffractometer (Siemens A G, Wittelsbacherplatz 2, Munchen D-80333, Germany) under the following experimental conditions: Cu anode; Wavelength 1: 1.54056; Wavelength 2: 1.54439; (Rel. Intensity): 0.500; Range 1—coupled: 3.000 to 40.000; Step Size: 0.040; Step Time: 1.0; Smoothing Width: 0.300; Threshold: 1.0.

The compound 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide may be prepared according to the methodologies disclosed in the aforementioned U.S. Pat. Nos. 6,107,329, 6,277,877, and 6,297,269.

EXAMPLE 1

5-Chloro-N-[(1S,2R)-3-[3R,4S]-3,4dihydroxy-1-pyrrolidinyl]-2-hydroxy-3-oxo-1-(phenylmethyl)propyl]-1H-indole-2-carboxamide Form A

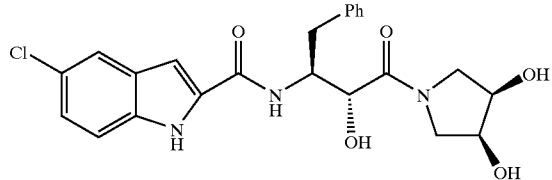

A 5.00 g sample of the Form D crystal form (the title compound of Examples 5, 6, and 6a hereinbelow) was charged into a reactor containing ethyl acetate (100 ml, 20 ml/g) at a temperature between 70° C. and 80° C., and the mixture was azeotropically distilled to remove water. Approximately 60 ml of ethyl acetate were removed to provide a thick white suspension. The suspension was cooled to ambient temperature, the mixture was filtered, and the residual product was dried in vacuo at ambient temperature to provide a total of 3.83 g (76.6% yield) of the desired Form A crystal form.

EXAMPLE 1a

5-Chloro-N-[(1S,2R)-3-[3R,4S]-3,4dihydroxy-1-pyrrolidinyl]-2-hydroxy-3-oxo-1-(phenylmethyl)propyl]-1H-indole-2-carboxamide Form A

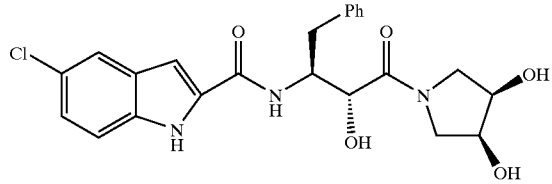

A 200 g sample of the Form C crystal form (the title compound of Example 4 hereinbelow) (30–40% ethanol wet) was combined with 2 L of ethyl acetate (10 ml/g), and the mixture was heated to between 70° C. and 78° C. Approximately 1.5 L of ethanol/ethyl acetate was distilled off to furnish a thick white slurry. Additional ethyl acetate (300 ml) was added, the resulting mixture was allowed to cool to between 15° C. and 25° C., and then stirred for about 24 hours. The formed solid was collected by filtration, washed with ethyl acetate (200 ml), and dried in vacuo at ambient temperature for about 24 hours to provide a total of 95 g of the title Form A crystal form.

EXAMPLE 2

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide

FORM B

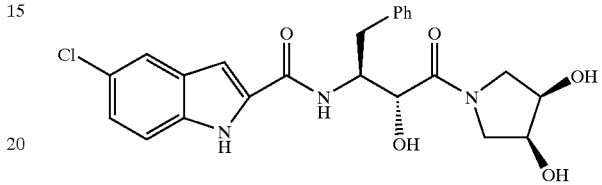

A clean, dry, 300-gallon glass-lined reactor was charged with 61.7 kg of the Form D crystal form (the title compound of Examples 5, 6, and 6a hereinbelow), 433 L of ethyl acetate, and stirring was commenced. The mixture was adjusted to a water content of between 1.5 and 2.5% water, and stirring continued at a temperature of between 22° C. and 26° C. The resulting solution was rendered free of trace particulate matter by filtration through a 1 μm filter into a clean tank. The solution was treated with Form B seed crystals (~100 g) and then stirred for 15 minutes. The mixture was then warmed for about 12 hours at a temperature of about 74° C. to provide a slurry. After removal of a small amount of ethyl acetate/water by azeotropic distillation, the slurry was cooled and stirred at room temperature. The product was collected by suction filtration, washed with ethyl acetate, and dried under vacuum at a temperature of between 40° C. and 50° C. to give 56.9 kg (99.5% yield) of the pure Form B crystal form. HPLC (Kromasil® C4; 250 mm column; 1.0 ml/min.; 55/45 0.1% $HClO_4$ buffer/acetonitrile) indicated the product to be 99.5% pure.

EXAMPLE 3

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide

FORM B

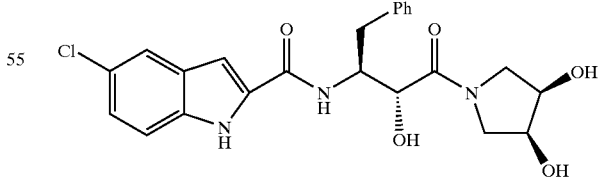

A 4.00 g sample of the anhydrous Form A crystal form (the title compound of Examples 1 and 1a hereinabove) was charged into a reactor together with ethyl acetate (40 ml, 10 ml/g), and water (0.6 ml). The mixture was heated to reflux, and held at this temperature for about 24 hours. The suspension was cooled to about 25° C., and the mixture was stirred for about one hour. The solid was collected by filtration, and dried in vacuo for about 24 hours to furnish a total of 2.86 g (71.5% yield) of the desired Form B crystal form.

Where desired, and/or appropriate, the anhydrous Form B crystal form, prepared as described hereinabove in Examples 2 and 3, may be purified according to the following procedure.

A clean, dry, 300-gallon glass-lined reactor was charged with 56.9 kg of the anhydrous Form B crystal form, 171 L of tetrahydrofuran, and 171 L of ethyl acetate, and stirring was commenced at a temperature of between 22° C. and 26° C. The mixture was adjusted to a water content of between 4.0 and 5.0% with water, and stirring was continued. The resulting solution was rendered free of trace particulate matter by filtration through a 1 μm filter into a clean tank. The tetrahydrofuran was atmospherically displaced with 662 L of ethyl acetate and the water content was adjusted to between 1.5 and 2.5% with water. The solution was treated with Form B seed crystals (~100 g) and then stirred for about one hour. The crystal form conversion was then warmed for about 12 hours at about 74° C. to provide a slurry. After removal of a small amount of ethyl acetate/water by azeotropic distillation, the slurry was cooled and stirred at room temperature. The product was collected by suction filtration, washed with ethyl acetate, and dried under vacuum at 40° C. to 50° C. to give 54.6 kg (96% yield) of pure Form B crystal form. HPLC (Kromasil® C4; 250 mm column; 1.0 ml/min.; 55/45 0.1% HClO$_4$ buffer/acetonitrile) indicated the product to be 99.7% pure.

EXAMPLE 4

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, Mono-ethanolate Form C

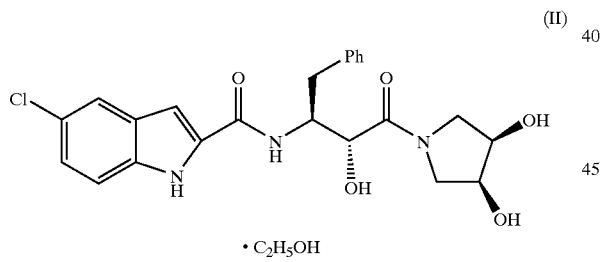

(II)

· C$_2$H$_5$OH

A 65 kg sample of 5-chloro-N-[(1S,2R)-3-[3R,4S]-3,4-dihydroxy-1-pyrrolidinyl]-2-hydroxy-3-oxo-1-(phenylmethyl)propyl)-1H-indole-2-carboxamide was dissolved in 600 L of ethyl acetate and the solution was vacuum stripped to a volume of about 300 L. To the solution was added 210 L of ethanol and the solution was vacuum stripped back to a volume of about 300 L. The ethanol displacement procedure was repeated an additional three times for a total charge of about 833 L of ethanol. The volume following the final vacuum stripping was about 425 L. A thick white suspension formed at the end of the distillation, and the resulting slurry was stirred overnight at ambient temperature. The solid was slowly collected by filtration, and the resulting filter cake was washed with ethanol (1×40 L, and 1×19 L). The resulting solid was blown dry with nitrogen for about three days to furnish 83.2 kg of the Form C crystal form.

EXAMPLE 5

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, Dihydrate Form D

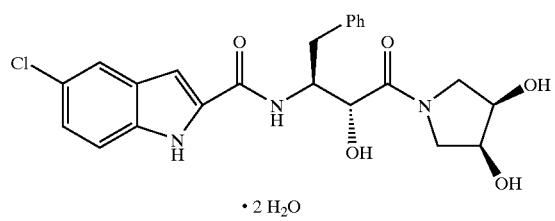

· 2 H$_2$O

A 2.50 g sample of the anhydrous Form A crystal form (the title compound of Examples 1 and 1a hereinabove) was charged into a reactor together with ethyl acetate (25 ml, 10 ml/g), and water (3.5 ml). The mixture became a solution at a temperature of 20° to 25° C. The mixture was then warmed to between 40° and 45° C., and hexanes (25 ml) was added over a period of about 15 minutes. The mixture was cooled to 20° C. over 30 minutes, and then stirred at ambient temperature for about 90 minutes. The solution was seeded with Form D seed crystals (~20 mg) to yield a suspension which was stirred at ambient temperature for about 30 minutes. The solids were collected by filtration, and dried in vacuo to furnish a total of 2.28 g of the desired Form D crystal form.

EXAMPLE 6

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, Dihydrate Form D

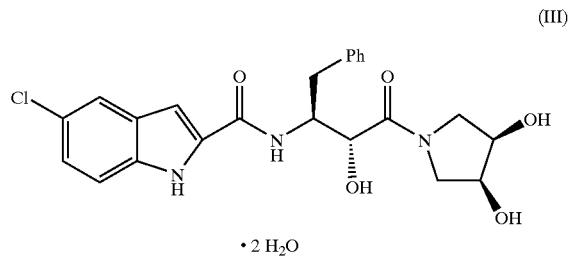

(III)

· 2 H$_2$O

A 2.50 g sample of the anhydrous Form B crystal form (the title compound of Examples 2 and 3 hereinabove) was charged into a reactor together with ethyl acetate (25 ml, 10 ml/g), and water (3.5 ml). The mixture was then warmed to between 40° and 45° C. to provide a complete solution. Hexanes (25 ml) was then added over a period of about 15 minutes. The mixture was then cooled to about 20° C. over 30 minutes, and then stirred for 90 minutes. The solid was collected by filtration, and dried in vacuo to provide a total of 2.31 g of the desired Form D crystal form.

EXAMPLE 6a

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, Dihydrate Form D

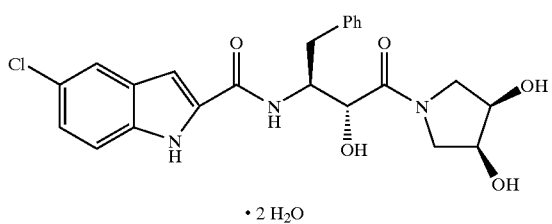

(III)

· 2 H₂O

A 200 g sample of the Form C crystal form (the title compound of Example 4 hereinabove) (30–40% ethanol wet) was combined with 2 L of ethyl acetate (10 ml/g). The mixture was then heated to between 70° C. and 78° C., and approximately 1.5 L of ethanol/ethyl acetate was distilled off at atmospheric pressure. Fresh ethyl acetate (500 ml) was added, and the distillation was continued, collecting an additional distillate volume of about 400 ml. The temperature of the solution was allowed to cool to about 40° C., and water (23 ml) was added to the solution to provide a final water content of about 2.5% to about 3% by weight. Hexanes (600 ml) was added to the solution over a period of about one hour, during which time the temperature of the solution was allowed to cool from about 40° C. to ambient temperature. The slurry was stirred for about one hour, the solid was isolated by filtration, and air-dried to furnish a total of 121 g of the desired Form D crystal form.

EXAMPLE 7

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, Hemi-ethanolate Form E

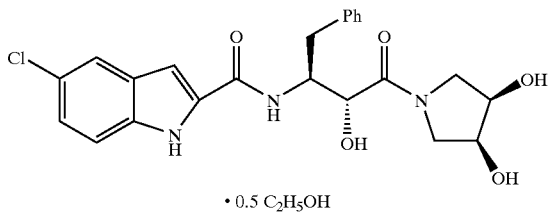

(IV)

· 0.5 C₂H₅OH

A 3.7 kg sample of 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide was dissolved in 17 L of ethyl acetate and the solution was washed with 11 L of water. To the ethyl acetate layer were added 61 grams of decolorizing charcoal and 100 grams of diatomaceous earth. The mixture was filtered over additional diatomaceous earth, the residue was rinsed with about 4 L of ethyl acetate, and the ethyl acetate solution was vacuum-stripped to a volume of about 8 L. To the solution was added 16 L of ethanol and the solution was vacuum-stripped to a volume of about 8 L. This ethanol displacement procedure was repeated an additional two times for a total charge of about 48 L. The volume following the final vacuum stripping was about 21 L. To the resulting thick white slurry was added 10 L ethanol, and the mixture was stirred overnight at room temperature. An additional 10 L ethanol was added, and the slurry was stirred at ambient temperature for about 75 hours. The solid was collected by filtration, and the resulting filter cake was washed with ethanol (1×3 L, and 1×2 L). The resulting solid was oven dried in vacuo at about 35° C. to furnish 2.5 kg of the desired Form E crystal form.

EXAMPLE 8

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, Monohydrate Form F

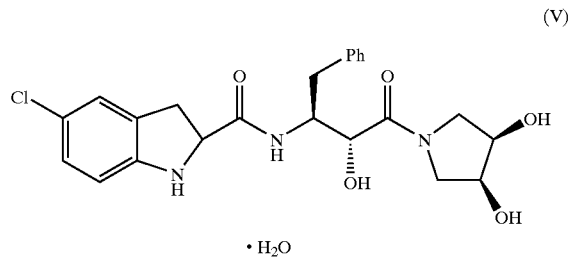

(V)

· H₂O

A 20 g sample of the Form D crystal form (the title compound of Examples 5, 6, and 6a hereinabove) was combined with 300 ml (15 ml/g) of methyl tert-butyl ether. Water (7.5 ml, 0.375 ml/g) was added, and the mixture was stirred at ambient temperature for about 18 hours. The resulting product was isolated by filtration, washed with 30 ml of methyl tert-butyl ether, and air dried at about 20° C. for about 24 hours to furnish 18.6 g of the title Form F crystal form.

EXAMPLE 9

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide Form G

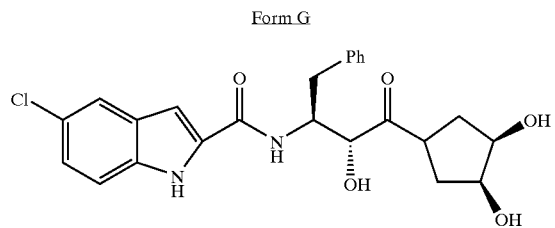

A 0.05 g sample of the Form B crystal form (the title compound of Examples 2 and 3 hereinabove) was placed in a sample holder and heated from about 30° C. to about 220° C. at a rate of about 6° C. per minute. The sample began to melt at a temperature of about 208° C., with concomitant formation, and subsequent crystallization, of the Form G crystal form.

What is claimed is:

1. A crystal form of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form B), which crystal form comprises characteristic high intensity X-ray diffraction peaks at diffraction angles (2-theta) of about 10.08, 11.49, 17.59, 19.42, 19.75, 21.65, 22.91, 24.66 and 26.42, and X-ray diffraction d-spacings of about 8.77, 7.70, 5.04, 4.57, 4.49, 4.10, 3.88, 3.61, and 3.37, respectively.

2. A crystal form according to claim 1 which crystal form further comprises characteristic diffraction peaks at diffraction angles (2-theta), X-ray diffraction d-spacings (Å), and intensities (I) of about:

| Angle 2-Theta | d-value (Å) | I |
|---|---|---|
| 3.45 | 25.61 | 5.4 |
| 4.93 | 17.91 | 8.4 |
| 10.08 | 8.77 | 64.1 |
| 11.49 | 7.70 | 44.4 |
| 13.22 | 6.69 | 17.3 |
| 15.21 | 5.82 | 23.7 |
| 15.79 | 5.61 | 14.6 |
| 16.75 | 5.29 | 22.3 |
| 17.27 | 5.13 | 31.2 |
| 17.59 | 5.04 | 93.2 |
| 18.00 | 4.92 | 35.5 |
| 18.28 | 4.85 | 20.4 |
| 18.91 | 4.69 | 30.2 |
| 19.42 | 4.57 | 54.7 |
| 19.75 | 4.49 | 55.1 |
| 20.08 | 4.42 | 20.1 |
| 21.15 | 4.20 | 8.4 |
| 21.65 | 4.10 | 52.5 |
| 22.91 | 3.88 | 100.0 |
| 23.72 | 3.75 | 10.7 |
| 23.95 | 3.71 | 15.8 |
| 24.66 | 3.61 | 68.4 |
| 26.42 | 3.37 | 74.6 |
| 26.93 | 3.31 | 14.5 |
| 27.58 | 3.23 | 21.2 |
| 28.46 | 3.13 | 19.2 |
| 29.02 | 3.07 | 26.8 |
| 30.61 | 2.92 | 14.8 |
| 31.13 | 2.87 | 8.3 |
| 32.27 | 2.77 | 17.4 |
| 33.10 | 2.70 | 6.7 |
| 33.60 | 2.67 | 9.1 |
| 34.10 | 2.63 | 16.3 |
| 34.90 | 2.57 | 7.8 |
| 35.56 | 2.52 | 6.9 |
| 35.95 | 2.50 | 6.5 |
| 36.55 | 2.46 | 8.5 |
| 36.96 | 2.43 | 5.2 |
| 37.78 | 2.38 | 5.0 |
| 38.88 | 2.31 | 5.7 |
| 39.40 | 2.29 | 5.8. |

3. A process for preparing anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form B), which process comprises the steps of:
(a) adding water to a suspension of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form A), or 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, dihydrate (Form D) crystal forms, in an aprotic solvent such that a water content of between about 0.5% and about 5.0% is achieved, and said Form A or said Form D crystal form is substantially dissolved to form a solution; and
(b) allowing said Form B crystal form to crystallize from said solution.

4. A process according to claim 3, wherein said water content is between about 1% and about 5%.

5. A process according to claim 3, wherein said aprotic solvent is selected from the group consisting of ethyl acetate, tetrahydrofuran, or a mixture of ethyl acetate and a non-polar, ethyl acetate-miscible co-solvent.

6. A process according to claim 5, wherein said aprotic solvent is ethyl acetate.

7. A process according to claim 3, wherein said crystallization of said Form B crystal form from said solution is facilitated by heating.

8. A process for purifying anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form B), which process comprises the steps of:
(a) heating a suspension of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (Form B) in an aqueous solvent system comprising:
(i) tetrahydrofuran and an aprotic, substantially tetrahydrofuran-miscible co-solvent; and
(ii) about 3% to about 8% water; such that said Form B crystal form is substantially dissolved to form a solution; and
(b) heating said solution to substantially remove aqueous tetrahydrofuran and crystallize said Form B crystal form.

9. A process according to claim 8, wherein said tetrahydrofuran and said aprotic, substantially tetrahydrofuran-miscible co-solvent are present in about a 1:1 (v/v) ratio.

10. A pharmaceutical composition comprising a or Form B crystal form of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide according to claim 1, and a pharmaceutically acceptable carrier, vehicle, or diluent.

11. A method of treating a glycogen phosphorylase dependent disease or condition which method comprises administering to a mammal in need of such treatment a Form B crystal form of anhydrous 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide according to claim 1, or a pharmaceutical composition comprising such Form B crystal form.

12. A method according to claim 11, wherein said glycogen phosphorylase dependent disease or condition is selected from the group consisting of hypercholesterolemia, hyperglycemia, hyperinsulinemia, hyperlipidemia, hypertension, atherosclerosis, diabetes, diabetic cardiomyopathy, infection, tissue ischemia, myocardial ischemia, and tumor growth.

* * * * *